United States Patent [19]

Dragan

[11] Patent Number: 4,569,662
[45] Date of Patent: Feb. 11, 1986

[54] BULK CARTRIDGE FOR PACKAGING AND DISPENSING A DENTAL MATERIAL

[76] Inventor: William B. Dragan, 85 Burr St., Easton, Conn. 06430

[21] Appl. No.: 626,492

[22] Filed: Jun. 29, 1984

Related U.S. Application Data

[62] Division of Ser. No. 314,768, Oct. 26, 1981, Pat. No. 4,472,141.

[51] Int. Cl.⁴ ............................................. A61C 5/04
[52] U.S. Cl. ................................................... 433/89
[58] Field of Search ..................... 433/90, 81; 604/232

[56] References Cited

U.S. PATENT DOCUMENTS

| | | | |
|---|---|---|---|
| 3,581,399 | 1/1971 | Dragan | 433/90 |
| 4,138,816 | 2/1979 | Warden | 433/90 |
| 4,457,712 | 7/1984 | Dragan | 433/90 |

*Primary Examiner*—John J. Wilson

*Attorney, Agent, or Firm*—Arthur T. Fattibene

[57] ABSTRACT

A dental syringe for the dispensing of a relative viscous dental material that includes a readily replaceable barrel portion that defines a reservoir for containing a bulk supply of a dental material having a spout or nozzle discharge end to which a dispensibly nozzle tip is detachably connected and which barrel portion is sealed by a displaceable plug. A plunger is provided for effecting the displacement of the plug for effecting the extruding of the material from the barrel portion as needed, and which plunger has formed on the end thereof a unidirectional vent arrangement which is operative for imparting a negative pressure on the end plug to permit a slight rearward displacement thereof to relieve the back pressure exerted on the plug by the material upon the termination of an extruding operation and thereby prevent drooling of any unwanted material subsequent to an extruding operation.

1 Claim, 27 Drawing Figures

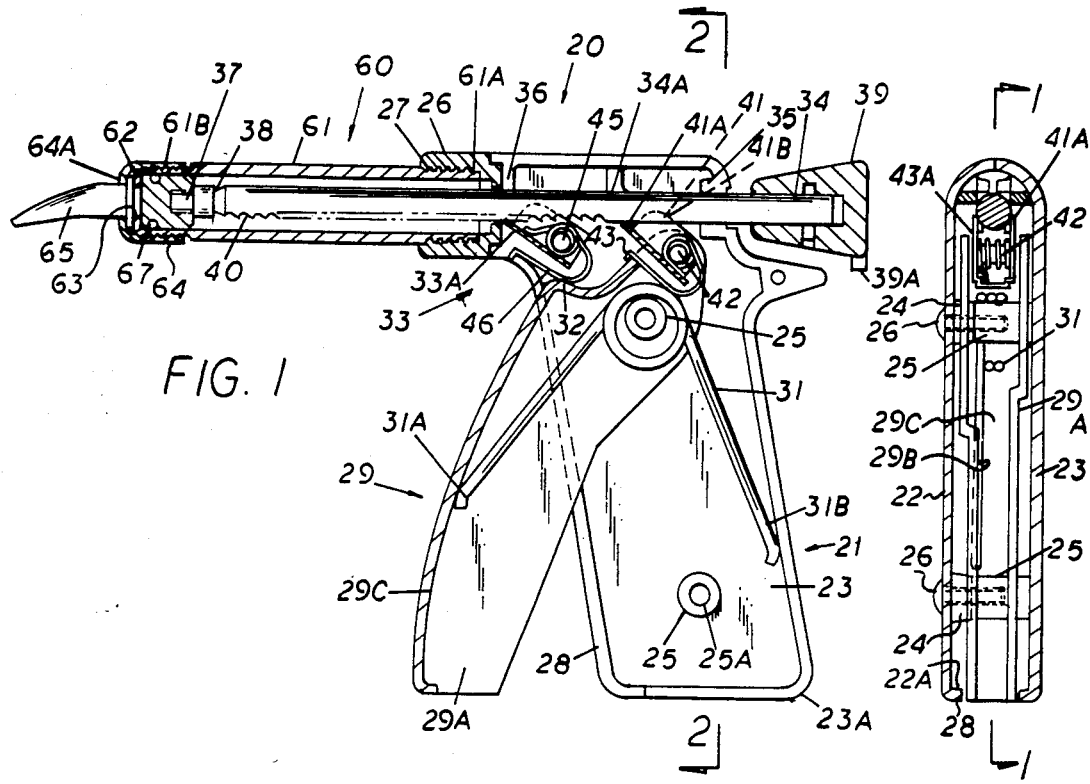
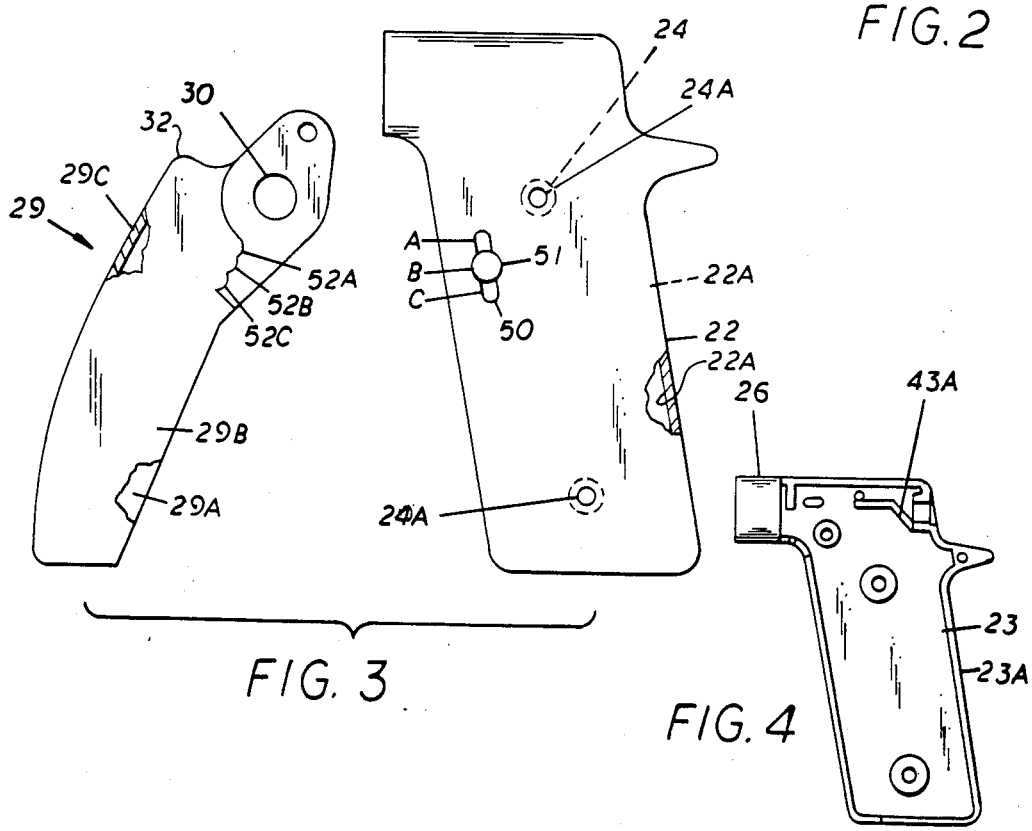

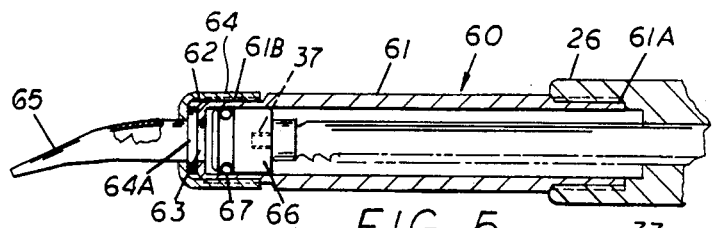
FIG. 5
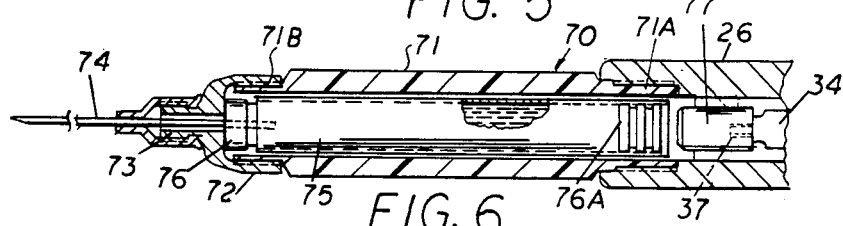
FIG. 6
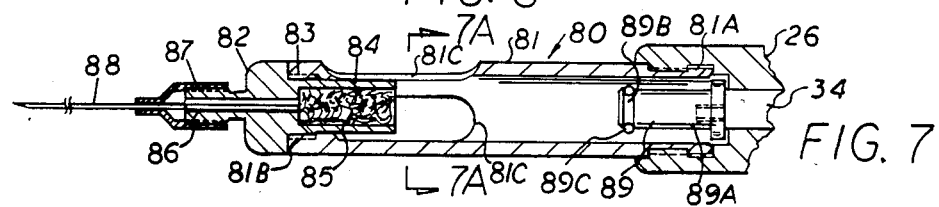
FIG. 7
FIG. 7A  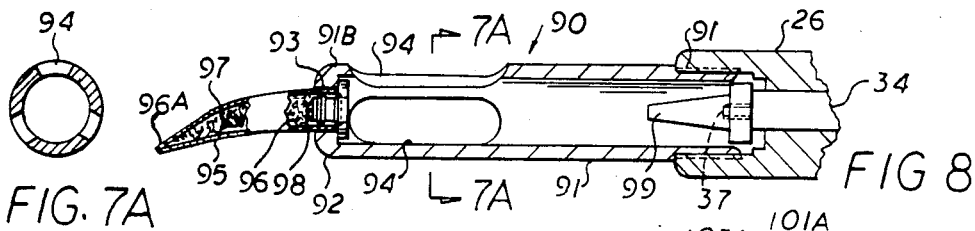 FIG. 8
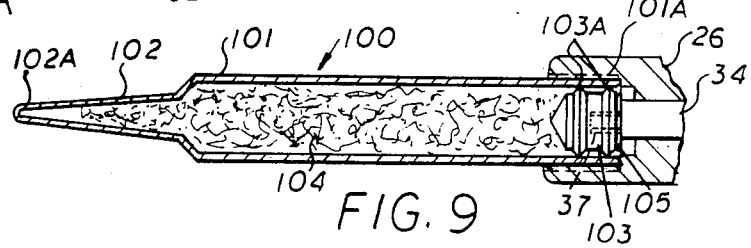
FIG. 9
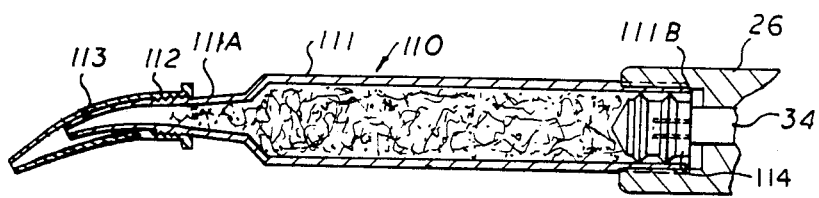
FIG. 10
FIG. 11  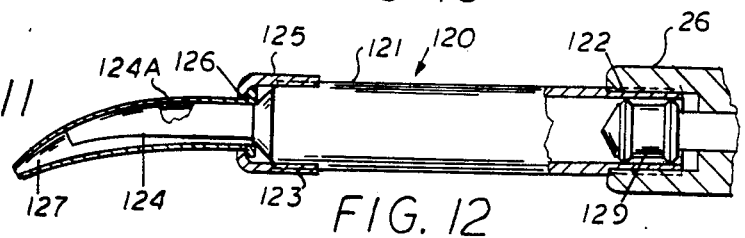 FIG. 12

BULK CARTRIDGE FOR PACKAGING AND DISPENSING A DENTAL MATERIAL

RELATED APPLICATION

This application is a division of my co-pending application, Ser. No. 314,768 filed Oct. 28, 1981, entitled All Purpose Dental Syringe, now U.S. Pat. No. 4,472,141 issue 9-18-84.

PROBLEMS AND PRIOR ART

This invention relates to improvements in dental syringes, and more particularly to improvements to the dental syringes disclosed in my prior U.S. Pat. Nos. 3,436,828; 3,581,399; 3,900,954; 4,198,756; D-224,655 and pending patent application Ser. No. 251,278 filed Apr. 6, 1981.

Heretofore various known techniques and implements have been used by dentists to deliver or handle a particular dental material as may be required for the various known dental procedures. However, prior to this invention each type of material used in the various dental procedures requires its own specialized delivery or handling tool or instrument. For example, a particular type of anesthesis syringe was required to administer an anesthesia. Another implement or tool was required to deposit a filling material in a cavity. Root canal work required completely different sets of implements. In still other procedures, such as the taking of impressions, other types of implements or tools were required. As a result a dentist needs a host of varying types and kinds of implements, syringes, tools, spatulas and the like to perform and/or otherwise administer or handle the various different kinds of dental materials required for the many and various dental procedures daily performed by such dentists. With the ever increasing advances in dentistry, new dental materials are being constantly developed, which require a new and more efficient means for the handling, administering or working with such material, e.g. the composite resins and the chemicals setting epoxies and/or light settable materials. The present invention has been developed so as to facilitate the handling and delivery of the various dental materials in a simple and expedient manner.

OBJECTS

It is therefore an object of this invention to provide for an improved all purpose delivery system or syringe which can be readily adapted to deliver or dispense a variety of different dental materials, e.g. anesthesia, root canal material, various filling materials and/or composite resins, light setting material, impression material, and the like, thereby substantially reducing the number of tools or implements otherwise required to effect the delivery of such materials.

Another object is to provide an all purpose dental syringe which is relatively simple in construction, can be readily manufactured, and which is positive in operation.

Another object is to provide an all purpose dental syringe in which the components required to effect the delivery of a particular material are interchangeable with respect to a common power handle.

Another object is to provide for a multi-purpose dental syringe in which the component parts are color coded for ease of assembly and use.

Another object is to provide an all purpose dental syringe in which the amount of the various materials dispensed thereby can be varied or adjusted according to need or desire.

Another object is to provide a carrier for containing a supply of filling material for storing or shipping such material and which carrier functions as component of an all purpose syringe.

Another object is to provide a syringe in which the dispensing of a material due to any residual pressure imparted on the material is prohibited.

Another object is to provide an improved all purpose syringe for dispensing light setting filling material and a cartridge for such material.

SUMMARY OF THE INVENTION

The foregoing objects and other features of this invention are attained by an all purpose dental syringe for delivering various kinds of dental materials as may be required for the various dental procedures. The all purpose syringe comprises a power handle to which a plurality of barrel assemblies are interchangeably connected and each barrel assembly being adapted to dispense a different type of of dental material, e.g. an anesthesia, composite resin, root canal material, impression material, hydrocolloid, chemical setting epoxies, light setting material and the like. The power handle includes a pair of complementary handle sections having a spring bias trigger mounted therebetween. A plunger is reciprocally mounted in the power handle and a drive pawl is operatively associated with the trigger to effectively advance the plunger as the trigger is activated. A holding pawl is cooperatively associated with the plunger to prohibit any backlash of the plunger as the drive pawl is retracted upon the release of the trigger. An adjustment is associated with the trigger to vary the throw thereof and thereby regulate the linear advance of the plunger during a dispensing operation to control or vary the amount of material dispensed.

The interchangeable barrels and the respective component parts are constructed to accommodate a particular dental material. Complementing the respective barrels is a plunger tip arranged to detachably connect to the plunger thereby adapting the plunger to extrude the material dispensed by a particular barrel. By attaching the barrel containing the appropriate material to the common power handle, a dentist can effect the delivery of any of several distinct dental materials with essentially the same instrument or syringe. In one embodiment the barrel is particularly constructed for dispensing and storing a supply of light setting material in a manner which prohibits the setting up of the material until it has been delivered. Another embodiment prohibits dribbling or dispensing of the material from the nozzle due to residual pressure imparted on the material after an extruding operation.

FEATURES

A feature of the invention resides in the provision of an all purpose dental syringe which comprises a power handle to which a plurality of interchangeable barrels can be readily connected to effect the dispensing of a variety of different types of dental materials which may be required for various dental procedures.

Another feature resides in the provision of an improved carrier or cartridge construction particularly adapted for storing and dispensing a light settable material and/or other type of dental and/or medical materials.

Another feature resides in a general purpose syringe which is capable of dispensing both liquid and solid materials.

Another feature resides in a general purpose syringe which can be readily adapted to dispense a variable proportion of dental materials as may be desired.

Another feature resides in the provision of providing a dental syringe with interchangeable barrels and complementary plunger tips which are interchangeable on a common power handle having a sufficient mechanical advantage to effect the dispensing of a relatively viscous material through a relatively small gauge needle with a minimum of effort.

Another features resides in the provision of a multiple purpose syringe having a power handle in the form of a piston grip to facilitate the use and operation thereof.

Another feature resides in the provision of a plunger which is constructed in a manner so as to co-act with the holding pawl in a manner so as to prohibit unintentional removal of the plunger from the handle portion of the syringe.

Other features and advantages will become more readily apparent when considered in view of the drawings and detailed description in which FIG. 1 is a side sectional view of the all purpose syringe embodying the invention taken on line 1—1 on FIG. 2.

FIG. 2 is an end sectional view taken generally along line 2—2 on FIG. 1.

FIG. 3 is a partial exploded side view of a handle section and associated trigger.

FIG. 4 is a partial plan view of the other handle section.

FIG. 5 is an enlarged side sectional view of the syringe barrel assembly for dispensing a dental impression material.

FIG. 6 is a side sectional view of a syringe barrel assembly for dispensing a dental anesthesia or hydrocolloid.

FIG. 7 is a side sectional view of a syringe barrel assembly for dispensing a root canal material.

FIG. 7A is a sectional view taken on line 7A—7A on FIG. 7 and on FIG. 8.

FIG. 8 is a side sectional view of a syringe barrel assembly for dispensing a composite resin filling material.

FIG. 9 is a side sectional view of a syringe barrel assembly for dispensing a light settable dental material or orthopedic cement.

FIG. 10 is a side sectional view of a modified syringe barrel assembly.

FIG. 11 is a detail sectional view of a sealing cap for use with the syringe barrel assembly of FIGS. 9 and 10.

FIG. 12 is a side sectional view of another barrel assembly.

DETAILED DESCRIPTION

Figure 18:
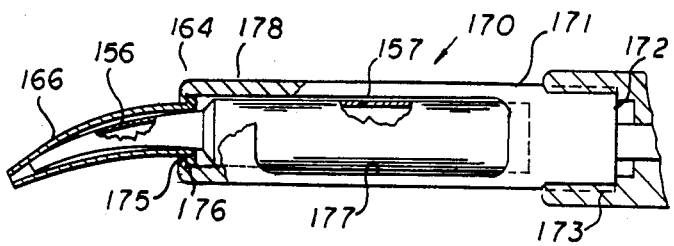
FIG. 18 is a side elevation view of another barrel assembly having parts shown in section.

Referring to the drawings, there is best seen in FIG. 1 an all purpose dental syringe 20 which, as will be herein described, can be utilized to dispense virtually all of the currently, commonly used, dental materials as may be required in the performance of various dental procedures. For example, the syringe 20 may be used to inject an anesthesia; it can be used to dispense and position dental impression material which may be a viscous rubber like material; it can be used to dispense a root canal material in a minute root canal; it can be used to dispense a composite resin material to restore a tooth, it can be used to store or dispense light settable dental material, it can be used to dispense a hydrocollid, and other flowable materials. The dental syringe 20 comprises essentially of a power handle 21 to which a plurality of readily interchangeable barrel assemblies can be attached, e.g. the various barrel assemblies shown in FIGS. 5 to 18, as will be hereinafter described. Each barrel assembly is constructed to effect the dispensing of a given material, and each barrel assembly is constructed to detachably connect to the power handle 21.

In the illustrated embodiment the power handle 21 is defined by a pair of complementary handle sections 22 and 23, which are generally similar in outline, but opposite in hand. The respective handle sections 22 and 23 can be formed generally of a suitable casting or stamping, or molded in the shape of a pistol grip. Each handle section 22 and 23 is provided with a circumscribing flange 22A, 23A which when assembled mate with one another. As best seen in FIG. 2, each section is provided with a pair of complementary bosses 24, 25 which when assembled are disposed in alignment. One boss, e.g. boss 25 is provided with a tapped hole 25A and the other boss 24 formed with a drilled hole 24A. A screw fastener 26 extended through the aligned bosses 24, 25 secures the respective handle sections in assembled position. Referring to FIGS. 1 and 4, the handle section 23 has connected to the upper end thereof a barrel mount 26. The barrel mount 26 is defined as an annular ring or collar which is integrally connected to one of the handle sections and which is internally threaded at 27. The respective handle sections 22, 23 are formed so that in the assembled position the front end of the assembled power handle 20 is provided with an opening 28 for accommodating a trigger 29. The trigger comprises an elongated member having a pivot hole 30 extending therethrough. The trigger 29 in the assembled position of the handle 20 is pivotably disposed between the handle sections 22, 23 by extending the upper bosses 24, 25 through the pivoting hole 30. A pig tail spring 31, coiled about the upper aligned bosses 24, 25; and having its respective ends 31A and 31B biased against the trigger 29 and the rear wall of the assembled handle sections, maintains the trigger under a spring bias. As best seen in FIG. 2, the trigger 29 is defined as a generally U-shaped member in cross section having spaced apart side flange portions 29A, 29B and an interconnecting front web portion 29C. The trigger adjacent its upper end is provided with a shoulder 32 which is disposed opposite to a holding pawl means 33. The holding pawl means 33, as will be hereinafter described, functions to prohibit any backlash of the plunger 34, and it also functions to prohibit any unintentional separation of the plunger 34 from the handle 20 when the plunger is retracted.

The respective flanges 22A and 23A of the respective handle sections are further provided with aligned bearing portions 35 and 36 for accommodating the plunger shaft 34A of plunger 34. The arrangement is such that the plunger shaft is reciprocally mounted within the aligned bearing portions 35 and 36. The leading end of the plunger shaft 34 terminates with a threaded nipple or tip 37. Immediately adjacent the threaded tip 37 is an annular limit or stop groove 38. The other end of the plunger shaft is provided with a pull knob 39. Longitudinally spaced along a lower circumferential portion of the plunger shaft 34A are a series of ratchet teeth 40. The arrangement is such that the plunger shaft is freely rotatable within its bearing mounts 35 and 36 so that the ratchet teeth 40 can be rotated into and out of engagement with a drive means as will be hereinafter described. If desired, the pull knob may be provided with an indicator or projection 39A to indicate the relative position of the ratchet teeth to its drive means.

The drive means for effecting the incremental advance of the plunger 34 comprises a ratcheting pawl 41. The ratcheting pawl is pivotably mounted between the flange portions 29A and 29B of the trigger 29 about a pivot pin 42. A pawl spring 43 is coiled about the pivot pin 42 with its ends disposed so as to normally bias the ratchet end 41A of the pawl into engagement with the teeth 40 of the plunger. In the illustrated embodiment the ratchet pawl 41 includes a side flange 41B which follows an incline cam 43A formed on the internal surface of handle section 23, as best seen in FIG. 4. The riding of the ratchet side flange 41B on the inclined cam 43A functions as a means for effecting positive disengagement of the ratchet pawl 41 from the plunger ratchet teeth 40 upon the release of the trigger and when the trigger is in its normal inoperative position as seen in FIG. 1.

As will be evident in FIG. 1 each time the trigger is squeezed, i.e. move to the right as seen in FIG. 1, the upper end of the trigger is rotated counterclockwise about the pivot 25 causing the ratchet pawl to ride up cam 43A and engage the ratchet teeth 40 of the plunger 34 to advance the plunger to the left. In FIG. 1, the plunger 34 is illustrated in a maximum advanced position.

To prevent any backlash or tendency of the plunger 34 to retract upon the release of the trigger 29, a holding pawl means 33 is provided. The holding pawl means 33 includes a pawl 33A which is pivotably mounted between the handle sections about a pivot pin 45. A pawl spring 46 is coiled about the pivot pin 45 so that the ends of the spring 46 effect a bias on the pawl 33A to normally maintain it biased against the ratchet teeth 40. Thus when the trigger 29 is released to return the ratchet pawl 41 to its inoperative position as shown in FIG. 1, the holding pawl 33A will prohibit any retraction or backlash of the plunger 34.

The power handle is also provided with a means for adjusting the throw of the trigger and thereby control the linear advance of the plunger 34 each time the trigger is squeezed. As it will become evident hereinafter, the amount of plunger advance will control the amount of dental material to be dispensed. The adjusting means comprises an elongated slot 50 formed in the handle section 22. A stop pin or buttom 51 is slidably disposed in slot 50. In the illustrated embodiment the stop pin or button has three adjusting positions; A, B and C. Co-operatively associated on the trigger 29 and adjacent the slot 50 are a series of detents or stops 52A, 52B, 52C. The detents or stops 52A, 52B and 52C correspond with pin positions A, B and C respectively. It will be apparent that in the assembled position the shifting of the pin 51 to positions A, B or C will engage the corresponding detent or stop 51A, 51B or 51C to limit the angular displacement of the trigger and thereby control the movement of the ratchet pawl 41 and the corresponding plunger advance accordingly. In the embodiment shown, maximum plunger advance is achieved when the slide pin 51 is disposed in Position A and that minimum plunger advance is had when the slide pin 51 is disposed in position C. Position B provides for an intermediate advance of the plunger 34.

In accordance with this invention a plurality of barrel assemblies are interchangeably connected to the barrel mount 26 of the power handle described. As will be described each of the barrel assemblies as shown in FIGS. 5 to 18 are constructed to hold and dispense a particular type of dental material depending upon a given dental procedure to be performed. The barrel assembly 60 as shown in FIG. 1 and in FIG. 5 is constructed to dispense a rubber base type or like impression material. Thus the barrel assembly 60 comprises an elongated tubular barrel 61 having a threaded end portion 61A which can be readily threaded to the barrel mount 26. The other end of the barrel 61 is also externally threaded at 61B. As best seen in FIG. 5, the end 61B of the barrel is provided with an inturned flange 62 to defend an end opening 63. An end collar 64 having a central opening 64A is threaded to the end 61B of the barrel. Extended through the opening 64A of the collar 64 is a dispensing nozzle or tip 65. The dispensing nozzle or tip is preferably formed of a readily expendible plastic material, and is similar to those tips disclosed in my prior U.S. Pat. Nos. 3,581,359 and D-224,655, but without the plug.

Connected to the end of the plunger shaft is a plunger tip 66 for complementing the barrel assembly 60. As shown the plunger tip 66 is provided with a diameter which snugly engages the internal walls of the barrel 61. A sealing O ring 67 may be provided so as to effect a positive seal with the internal walls of the barrel 60. The plunger tip 66 is threaded to the threaded tip 37 of the plunger shaft 34A as seen in FIG. 1.

In this embodiment it will be noted that the threaded end 61A is of a different size than the other threaded end 61B. Thus the arrangement is such that barrel 61 can only be threaded to the barrel amount with end 61A.

In operation, the entire length of the barrel 61 may be filled with an impression material, and with the plunger 34 disposed in its retracted position, the loaded barrel 61 can be readily fitted to the power handle. The disposable nozzle tip 65 is then fitted to the other end 61B of the barrel 61 by collar 64. With plunger tip 66 connected to the plunger shaft 34A the syringe 20 is ready to dispense a rubber base impression material by squeezing the trigger. With the ratchet teeth 40 of the plunger disposed in engagement with the ratchet pawl 41, the plunger is advanced to extrude the impression material through the nozzle 65 as the trigger 29 is squeezed. By adjusting the position of the pin stop 51, more or less of the impression material may be extruded depending upon the setting of the pin stop 51 upon each actuation of the trigger.

FIG. 6 is directed to a modified barrel assembly 70 which can be interchangeably connected to the barrel mount 26 of the power handle construction described with respect to FIGS. 1 through 4. The barrel assembly 70 when connected to the power handle 21 defines a dental syringe for injecting intralignmentary anesthesia. As shown the anesthesia barrel assembly 70 comprises an elongated tubular barrel 71 which may be formed of a transparent plastic material to provide visibility. One end of the barrel 71 is provided with a series of external threads as indicated at 71A whereby the barrel 71 can be readily connected to the barrel mount 26 of the power handle 21. The other end of the barrel 71 is externally threaded at 71B. Connected to end 71B of the barrel 71 is an end tip 72 which is provided with internal threads for mating to the threaded end 71B. Projecting from the front end of the tip 72 is a nipple 73 to which a conventional type anesthesia needle 74 can be readily connected and disconnected. The barrel 71 is sufficiently long so as to receive an anesthesia carpule 75 of standard construction. The standard anesthesia carpule 75 comprises an elongated glass envelope 75 containing the anesthesia and which is generally sealed at one end with a diaphragm 76, which is adapted to be perforated by the rear portion of the anesthesia needle 74 so as to place the needle 74 in communication with the anesthesia stored within the glass envelope 74A. The other end of the glass envelope is closed by a piston 76A, which is displaceable disposed within the envelope 75A of the carpule 75. To effect displacement of the piston 76A, the threaded tip end 37 of the plunger 34 has connected thereto a plunger tip 77 which is specifically shaped to engage the piston 76A so as to effect the displacement of piston 76A as the trigger 29 of the power handle is actuated, to advance the plunger 34. The anesthesia syringe as described with resect to FIG. 6 is such that the barrel 71 in addition to supporting the anesthesia carpule 75, also functions to confine the glass of envelope 75A of the carpule in the event that the glass envelope should break during the administration of the anesthesia. In the event of such accident, the patient is positively protected from broken glass. By setting the adjustment button 51 to positions A, B or C, the amount of anesthesia which is to be injected can be controlled accordingly by the dentist.

The anesthesia syringe as described with respect to FIG. 6 can also be readily utilized by the dentist to dispense a hydrocolloid. To adapt the anesthesia syringe barrel of FIG. 6 for dispensing a hydrocolloid, a hydrocolloid carpule and its associated needle is substituted for the anesthesia carpule 75 and its needle. Thus, the anesthesia syringe barrel assembly 71 as described can be effectively utilized to inject either an anesthesia or a hydrocolloid material for taking impressions.

FIG. 7 illustrates another modified barrel assembly 80 which is readily interchangeable with the other barrels herein described so as to define the syringe tool applicable for injecting a root canal material in the prepared root canal of a tooth during the root canal procedure. As shown in FIG. 7, the root canal barrel assembly so comprises an elongated tubular barrel 81 formed with external threads at one end 81A for threading to the barrel mount 26 of the power handle 21. The other end 81B of the barrel 81 is provided with internal threads to which a tip 82 is detachably connected. It will be understood that the tip 82 is provided with external threads 83.

In the illustrated form of the invention the tip 82 is provided at its rear end with a chamber portion 84 to define a reservoir for containing a supply of root canal material 85. The reservoir or chamber 84 is connected in communication to a passageway 86 which projects forward thereof and through the extended nipple portion 87 of tip 82. Connected to the end of the nipple 87 is a needle 88 which defines the dispensing nozzle for directing the root canal material disposed in in chamber 84 into the minute root canals of a tooth.

To extrude the root canal material 85 the plunger 34 has connected to the tip 37 end a plunger tip 89 which complements the reservoir chamber 84 as shown in FIG. 7. The plunger tip 89 is provided with a tapped hole 89A whereby it can be reaidly threaded to the trheaded tip 37 of the plunger 34. The other end of plunger tip is provided with an annular groove 89B for accommodating a sealing O ring 89C. It will be apparent that the O ring 89C is sized so as to be snugly received within the chamber 84 so that the material in advance of the plunger tip 89 is extruded through the needle 88, as the plunger is advanced into the reservoir 84.

In operation, the chamber or reservoir 84 in the tip end 82 of the barrel assembly is filled with the appropriate root canal material by the dentist and the tip attached to the barrel 81, as shown. As hereinbefore described the amount of material which can be extruded through the needle or nozzle 88 can be readily controlled by the dentist by setting the adjustment stop to position A, B or C. To provide additional visibility of the chamber 84, the barrel 81 is provided with a series of circumferentially placed slotted openings 81C. It will thus be apparent that barrel assembly 80 can be readily interchanged with barrel assemblies 60 and 70 for adapting syringe 20 for yet another dental procedure.

FIG. 8 illustrates another barrel assembly 90 which can be readily interchanged with the other barrels hereinbefore described to define a syringe for delivering a composite resin or other dental type cements during a restorative procedure. In FIG. 8, the barrel assembly 90 comprises an elongated tubular barrel 91 having one end 91A threaded externally so as to accommodate the threads of the barrel mount 26 the power handle 21. The other end of the barrel 91B is provided with an inturned flange 92 to define a front opening 23. The sides of the barrel 91 adjacent to the front end 91B are provided with a plurality of cirumferentially spaced breach openings 94, as best seen in FIG. 7A. Three such breach openings 94 are circumferentially spaced about the tip end of the barrel 91. Extended through the opening 93 of barrel 91 is a dispensing nozzle 95. The dispensing nozzle has a reservoir section 96 which communicates with a dispensing nozzle tip opening 96A. The nozzle tip 95 may be of the type as described in my U.S. Pat.

Nos. 3,581,399; 3,900,545 or Des 224,655. According to this invention, the composite resin or dental cement 97 is disposed within the nozzle tip. The rear open end of the nozzle 95 is sealed with a plug 98. The arrangement is such that the nozzle 95 can be readily inserted through opening 93 by passing it through any one of the side breach openings 94.

To effect displacement of the plug 98 to express the composite resin or cement from the nozzle 95, the tip end 37 of the plunger shaft 34 is provided with a plunger tip 99 which complements the nozzle 95. It will thus be apparent that as the plunger 34 is advanced toward the nozzle 95, that the plunger tip 99 will engage the plug 98 to force the composite resin or cement 97 ahead of it out through the dispensing orifice 96A.

FIG. 9 illustrates another modified barrel assembly 100 which can be readily adapted to the barrel mount 26 of the power handle 21 as hereinbefore described. In this form of the invention, the barrel assembly 100 includes an integrally molded or formed member which includes a barrel portion 101 and an integrally connected elongated nozzle portion 102. The end 101A of the barrel portion 101 is provided with a full open end that is externally threaded so as to accommodate the internal threads of the barrel mount 26. In the form of the invention disclosed in FIG. 9, the discharge end 102A of the elongated nozzle portion 102 can be initially sealed, as shown, or formed with a discharge orifice. In accordance with this form of the invention, the barrel portion 101 of barrel assembly 100 defines reservoir or chamber for containing the dental material 104. By making the barrel assembly 100 of a light impervious material or light opaque material, the barrel assembly 100 can be utilized for storing and dispensing a light settable type dental material. The rear or open end 101A is closed by an end plug 103, which may also be formed of a light opaque material to confine or seal the dental material 104 within the barrel portion 101. The end plug 103 can be provided with a tapped hole 105 in the rear end thereof to accommodate the threaded tip 37 of plunger 34 of the power handle when the barrel 100 is connected thereto. The end plug 103, as shown, is provided with a pair of spaced apart circumscribing wippers of flanges 103A which are disposed in sealing engagement with the internal walls of the barrel portion 101. While the dental material 104 confined within the barrel portion of barrel assembly 100 may comprise any type of dental material, by making the barrel assembly 100 of a light opaque material, the barrel assembly can be utilized for storing and dispensing a light settable material. With the construction disclosed in FIG. 9, the barrel assembly 100 can also be utilized as the carrier or container in which such dental materials, as hereinbefore described can be marketed, and the container thus becomes an operative component part of the syringe by which the material is dispensed. In such case the dentist can readily attach the barrel assembly 100 to the power syringe handle 20 hereinbefore described and by snipping the end 102A an appropriate orifice is formed through which the dispensing material 104 can be dispensed. A sealing cap 115, as shown in FIG. 11, provides the closure to reseal the discharge orifice defined by snipping end 102A.

FIG. 10 is another modified embodiment of a barrel assembly of the type illustrated in FIG. 9. As shown in FIG. 10, the barrel assembly 110 contains a barrel portion 111 similar to that described with respect to FIG. 9. Connected to the barrel portion 111 is an elongated nozzle 111A. The other end 111B of the barrel portion 111 is provided with a full open end which is externally threaded so as to complement the internal threads of the barrel mount 26 of the power handle syringe 20 as hereinabefore described. Adjacent to the tip end of the nozzle portion 111A there is provided a series of surrations or threads 112 to which there is detachably connected and frictionally secured a nozzle tip 113. An end plug 114 similar to end plug 103A of FIG. 9 seals the open end of the barrel portion 111 to confine the material within the barrel portion 111. The rear end of plug 114 is also provided with a tapped opening for receiving the threaded end 37 of plunger 34 when the barrel assembly 110 is connected to the barrel mount of the power handle hereinbefore described. It will be understood that the barrel assembly 112 can be utilized to contain the same dental materials as described with respect to the embodiment of FIG. 9. By forming the barrel assembly 110 of a light opaque material, the barrel assembly can be readily adapted for dispensing light settable materials. The dispensing nozzle 113, which is detachably connected to the nozzle end 112 of the barrel assembly 110, may be of the type described in my U.S. Patents hereinbefore noted. Such nozzles 113 are readily disposable and can be readily disposed after each use. Thus the barrel assembly 110 provides an arrangement whereby the barrel when connected to the power handle defines a syringe which can be used in performing procedures or different patients simply by attaching a new disposable nozzle 113 for each patient.

After use and during storage, the open end or orifice of the nozzle portion 102 and 111A of FIGS. 9 and 10 can be resealed by an end cap 115, disclosed in FIG. 11.

The barrel assemblies of FIGS. 9 and 10 may be formed of a plastic material and thus provide for a relatively inexpensive and disposable container for the and thus material disposed therein and which also functions as a syringe component.

FIG. 12 illustrates still a further modified barrel assembly 120. Barrel assembly 120, when formed of a light opaque or light impervious material and preferably of plastic, can be readily used as a container and dispenser for light settable materials. As shown, the barrel assembly 120 comprises a barrel portion 121 which is externally threaded at 122 with threads for complementing the threads of the barrel mount 26 of a power handle. Thus the barrel assembly 121 can be rendered detachably connected to the power handle as hereinbefore described. Adjacent the front end of the barrel portion 121 there is provided an external threaded portion 123. Projecting beyond the front end of the barrel portion 121 is an elongated nozzle portion 124. A threaded collar 125 having a front opening 126 is connected at 123 to the barrel portion 121. As shown, a disposable nozzle tip 127 extends through opening 126 of collar 125 so as to receive and accommodate the nozzle portion 124 of the barrel assembly 120. In the arrangement described with respect to FIG. 12, the disposable nozzle 127 together with nozzle portion 124 forms a double wall dispensing nozzle tip. The nozzle tip 127 also functions as a rotatably directional control tip for precisely directing the extrusion of the material from the barrel assembly 120. It will be apparent that the nozzle tip 127 can be rotated a full 360° within its opening 126 to precisely control the direction and deposit of the material extruded. Also, the nozzle 127 forms a protective nozzle for the nozzle portion 124. Materials contained within the barrel 121, which may be a light settable material, is a very viscous material. The bore 124A extending through the nozzle portion 124 relative to the diameter of the barrel forms a relative minute passageway. Therefore, when the material is extruded, the nozzle portion 124 is subjected to relatively large pressures which may cause the nozzle portion to rupture. The exterior nozzle tip 127 thus functions as a means for confining the material in the event the nozzle portion 124 should rupture during a dispensing operation. In the barrel assembly described, the nozzle tip 127 is positively attached to the front end of the barrel by collar 125. In addition to the threaded connection being herein described, it will be understood that other positive types of connections may be used such as a bayonet type connection or other secured mechanical connections may be utilized. With the construction described the readily removable and disposable exterior nozzle tip 127 also functions to prevent cross contamination between patients, and the curved outer nozzle 127 allows the dentist to accurately dispense the appropriate amount of material in small and/or difficult to reach areas.

It will be understood that after the syringe with barrel assembly 120 has been used, the nozzle 127 can be readily disposed and the open tip end of the nozzle portion 124 can be resealed with a sealing cap 115 of the type disclosed by FIG. 11. Thus the barrel assembly 120 comprises a relatively large tube for containing a relatively large supply of dental material which can be readily secured to the power portion or mounting portion 26 of the power handle to form a syringe as described with respect to FIGS. 1 thru 4; and provides a means for storing the material between uses.

The rear open end of the barrel portion 121 is closed by a plug 129 similar to that hereinbefore described. If desires, the end plug 129 may be provided with a tapped hole in the end thereof for receiving the threaded tip 37 of a plunger 34. As an alternative it will be understood that the tip 37 may be provided with a plunger tip (not shown) arranged to abut against the rear end of plug 127 to effect the displacement thereof during an extrusion operation instead of being connected thereto.

Figure 13:
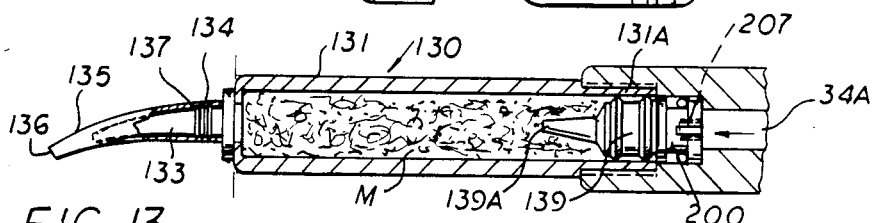
FIG. 13 is a side sectional view of a slightly modified embodiment of a barrel assembly and including a means to prohibit extruding material due to residual pressures.

FIG. 13 illustrates another modified barrel assembly 130 which may be interchangeably used in conjunction with the power handle to form the syringe. As shown in FIG. 13, the barrel assembly 130 comprises a barrel portion 131 which is fully open at one end 131A and has an elongated nozzle portion 133 integrally connected to the other end of the barrel portion 131. The end 131A of the barrel portion 131 is provided with an external thread 132 whereby the barrel assembly 130 can be readily attached to the mounting portion 26 of a power handle as hereinbefore described.

The elongated nozzle 133 is provided with a series of external threads 134 located adjacent the front end of the barrel. Detachably connected to the nozzle portion 133 is a dispensing nozzle or tip 135 which may be formed of a readily disposable material and which nozzle or tip 135 is similar to that disclosed in my U.S. patents hereinbefore cited. As shown the nozzle or tip 135 is provided with an angularly disposed discharged orifice 136. On the other or rear end of the nozzle or tip 135 there is provided an internal thread 137 adapted to complement the threads 134 on the nozzle portion 133. By mating the complementary threads 137 and 134, a positive means is provided for securing the nozzle 135 to the nozzle portion 133. It will also be understood that the nozzle 135 can be rotated through 360° so as to control the direction in which a dentist desires to direct the discharge orifice 136.

As disclosed in my U.S. patents herein cited, the disposable nozzle 135 is formed of a readily expendible thermo-plastic material. Such material can also be rendered self threading and therefore need not be provided with formed threads 137 as disclosed in FIG. 13. By maintaining the proper tolerances between the internal diameter of the nozzle 135 and the external threads 134, the nozzle 135 can be self threaded onto the nozzle portion 133. The open end of the barrel portion 131 is sealed by a plug 139 similar to that described with respect to FIG. 12, or may be provided with a projecting tip end 139A to displace material in the nozzle portion 133. In this form of the invention the disposable nozzle 135 functions in a manner similar to the nozzle 127, described with respect to FIG. 12. Nozzle 135 functions as a means for controlling the direction of dispensing the material stored within the barrel portion 131, as well as forming a double wall nozzle dispensing means to prevent any loss of material in the event that the inner nozzle portion 133 should rupture during an extruding procedure. Also, the disposable nozzle 135 provides a means for preventing cross contamination between patients.

Figure 14:
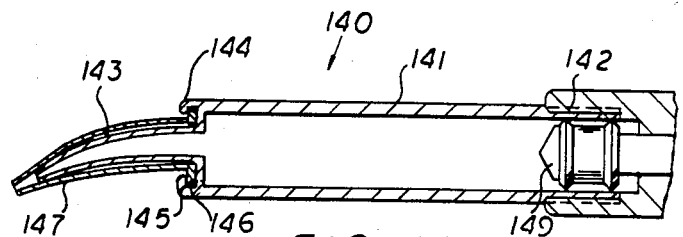
FIG. 14 is a side sectional view of another modified embodiment.

FIG. 14 illustrates still another modified barrel assembly. The barrel assembly 140 comprises a barrel portion 141 which is threaded at its rear end 142 whereby the barrel assembly 140 can be readily threaded into the barrel mount 26 of the power handle. The other end of the barrel is provided with an extended nozzle portion 143 similar to that hereinbefore described. The material to be dispensed is contained within the barrel portion 141 in a manner hereinbefore described. For storing a light settable material in the barrel assembly 140, it will be understood that the barrel assembly 140 is made of a light impervious or light opaque material.

In embodiment of FIG. 14, the front end 144 of the barrel portion 141 is provided with a circumscribing recessed portion 145 which is adapted to accommodate a laterally extending flange 146 which circumscribes the rear open end of a disposable nozzle 147 of the type described in my cited U.S. patents. As best seen in FIG. 14, the lateral flange portion 146 of a disposable nozzle 147 is snap fitted into the annular recess 145 so as to retain the nozzle 147 in position during an extruding operation. Because the material contained within the barrel portion 141 is generally a viscous material wich is extruded through a very narrow or small diameter passageway of the nozzle portion 143, extreme pressure is required. Therefore, a positive means must be provided for retaining the disposable nozzle 147 securely fastened to the front end of the barrel portion 141. The disposable nozzle 147 thus functions in a manner similar to that described with respect to FIGS. 12 and 13.

The rear end of the barrel portion 141 is sealed by an end plug 149 similar to that hereinbefore described.

It will be understood that the material contained within the barrel portions of the modifications disclosed in FIGS. 12, 13 and 14 may comprise composite resins, dental cement, light settable materials, impression material and other various materials used by dentists as may be required for the various dental procedures. It will also be understood that the barrel assemblies 120, 130 and 140 may be made of a disposable plastic material whereby the entire barrel assembly may be discarded upon the exhaustion of all the dental material carried therein. Also, while the power syringe and the various barrel assemblies herein disclosed and described are particularly adapted for use by a dentist, the power syringe; as described, may have application for use in other fields of endeavor. For example, the power syringe described can be utilized as an aid in orthopedic surgery for the placement of bone cement to aid in the cementing of certain orthopedic replacement parts such as hip joints. For surgical use the barrel assembly may be prepackaged in a sterile manner ready for use. The bone cement is mixed when the prosthesis is ready for cementing, and is placed into the large end of the barrel portion by the surgeon. The end plug is then placed in the end of the barrel portion and the tube assembly onto the power handle. The surgical material within the tube is then expressed in a manner as hereinbefore described.

Figure 15:
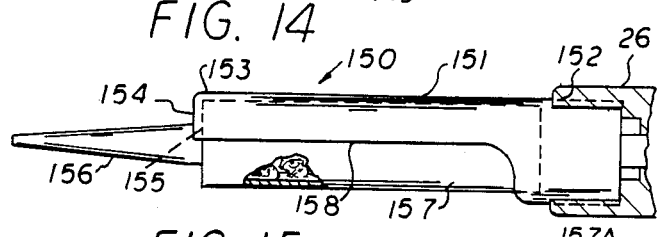
FIG. 15 is a side sectional view of another barrel assembly.
Figure 15B:
FIG. 15B is a sectional view taken on line 15B—15B on FIG. 15A.
Figure 15A:
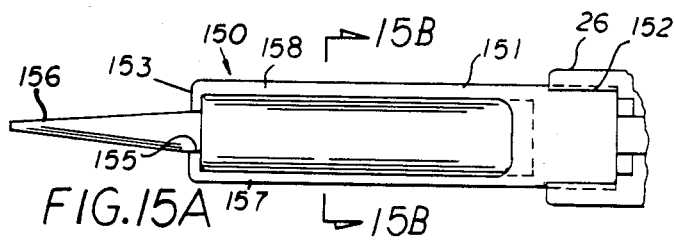
FIG. 15A is a bottom view of the barrel assembly of FIG. 15.

FIGS. 15, 15A, 15B and 15C illustrate another modified barrel assembly which can be interchangeably utilized with the power handle as hereinbefore described. The barrel assembly 150 of FIGS. 15, 15A and 15B is constructed so as to be utilized with a relatively large cartridge 157 adapted to be filled or prefilled with a dental material as hereinbefore described. In this form of the invention the barrel assembly 150 includes a tubular barrel 151 which is threaded at one end 152 whereby it can be readily secured to the barrel mount 26 of the power handle. The front end 153 of the tubular barrel 151 is provided with a front wall 154 having a slotted or arcuate shaped front opening 155 therein. Preferably the arcuate opening 155 is sized so as to receive and retain the nozzle portion 156 of a cartridge 157 as will be hereinafter described. The tubular barrel 151 is also provided with a side or breach opening 158 which is disposed in communication with the front opening 155 as best seen in FIG. 15A. It will be understood that the barrel portion 151 can be readily threaded or secured to the barrel mount 26 of the handle.

The barrel assembly 150, as described, is specifically arranged so as to receive a cartridge 157 which contains the dental material to be extruded. As shown the cartridge 157 comprises an elongated tubular body portion 157A which has a length greater than that of the breach opening 158 as best seen in FIG. 15A. The body portion 157A defines a reservoir which is open at its rear end 157B and which has connected to its other end an integrally connected elongated nozzle portion 156. As best seen in FIG. 15A, the cartridge 157 is inserted into the barrel 151 by first inserting the end 157B of the cartridge into the side opening 158 and then snap fitting the nozzle 156 in position through the arcuate front opening 155 as best seen in FIG. 15A. It will be understood that the end of the reservoir or body is sealed by an end plug 159 similar to that described with respect to FIG. 12, 13 and 14. With the material cartridge 157 disposed within the barrel portion 151 and the barrel portion secured to the barrel mount 26 of the power handle, the material in the cartridge 157 is readily expressed by squeezing the trigger of the power handle in a manner herein described. If desired, a disposable nozzle tip may be connected to the nozzle portion 156 similar to that described with respect to FIGS. 12 and 14. By disposing the disposable nozzle, which is similar to nozzles 127, 135 and 147, to the extended nozzle portion 156 will render the assembly of FIG. 15 operative in a manner described with respect to FIGS. 12 thru 14.

Figure 16:
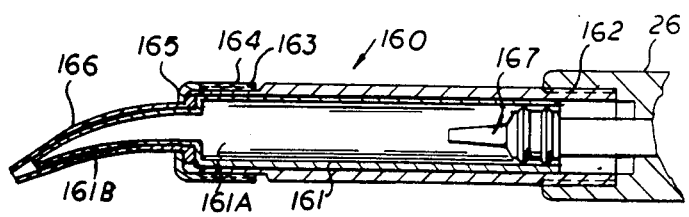
FIG. 16 is a side sectional view of another modified barrel assembly.

FIG. 16 illustrates another modified barrel assembly 160 for receiving a cartridge 161 containing a supply of dental material. As hereinbefore described the dental material contained within the body portion 161A of the cartridge 161 may comprise a composite resin, dental cement, light settable material, impression material or any like material used by a dentist during a dental procedure. For a cartridge containing a light settable material, it will be understood that such cartridge 161 be formed of a light impervious or light opaque material. The cartridge 161, as hereinbefore described, can be readily formed of a disposable plastic material so that when its content has been exhausted; the cartridge 161 may be disposed.

In this form of the invention, the barrel assembly 160 comprises an elongated tubular member to define a barrel which can be interchangeably connected to the barrel mount 26 of power handle of the type hereinbefore described. One end of the barrel is provided with a series of external threads 162 whereby it can be detachably connected to a barrel mount 26. The other end of the barrel is also provided with external threads 162. A flanged collar 164 having a front opening 165 is threadedly connected to threads 163. As shown, the cartridge 161 can be loaded through either end of the barrel 160. Integrally formed to the front end of the cartridge 161A is an elongated nozzle portion 161B. To provide directional control to the material being extruded during an extruding operation, a disposable nozzle or tip 166, similar to that hereinbefore described, is utilized to circumscribe the nozzle portion 161B of the cartridge 161. As shown the nozzle 166 is fitted over the nozzle portion 161B, and is retained to the end of the barrel by the collar 164. The arrangement is such that the nozzle 166 can be rotated a full 360° so as to give the dentist control over the direction in which the material is to be extruded. The rear end of the cartridge 161 is closed by an end plug 167. The end plug may be constructed similar to that described with respect to the end plugs of FIGS. 12 13, 14 and 15; or as an alternative construction, may be provided with an elongated projecting portion 167A arranged to extend into the nozzle portion 161B during the final stages of extrusion. By providing an elongated projection 167A on the end plug 167 the material which is otherwise confined to the nozzle portion 161B can be extruded therefrom and thereby minimizing the amount of waste otherwise necessitated. As hereinbefore described, the disposable nozzle 166 provides directional control in addition to functioning as a double walled nozzle, when utilized in conjunction with the nozzle portion 161B. Also the disposable nozzle 166 prevents cross contamination between patients.

Figure 17:
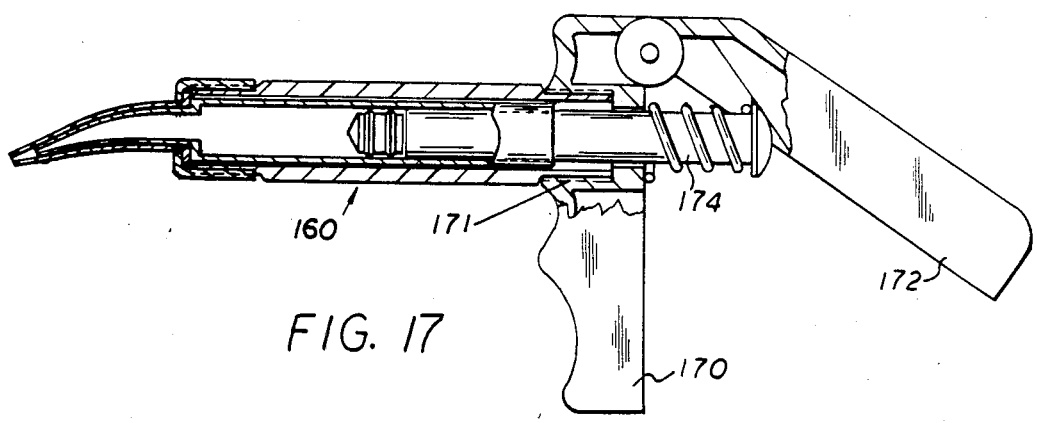
FIG. 17 illustrates a modified syringe embodiment, having parts shown in section.

The barrel assembly as described with respect to FIGS. 5 thru 18 and the associated cartridge 157, when used, as herein described can be readily adapted for use in a modified syringe handle construction as shown in FIG. 17. The handle construction shown in FIG. 17 comprises a first fixed handle portion 170 which has a threaded bore 171 disposed intermediate the ends of the handle portion 70. Pivotably mounted to the fixed handle portion 170 is a movable handle member 172. The barrel assembly and/or the barrel assembly including a cartridge containing the dental supply material as hereinbefore described can be readily detachably connected to the threaded bore 171. A plunger 174 extended into the rear end of the barrel to engage either the plug sealing the dental material within the barrel; or in the event of a cartridge, th plug sealing the rear end of the cartridge containing the dental material to effect the displacement thereof to extrude the material therefrom.

From the foregoing it will be apparent that this invention is directed to an improved syringe barrel and/or cartridge construction for storing and dispensing a dental material as for example composite resins, dental cements, light settable material, impression material, anesthesia, hydrocolloids and the like; and which supply of material can be incrementally dispensed in relatively small varying amounts as may be required. Also, such cartridges and/or barrel assemblies can be interchangeably used with a single, common syringe handle to define a syringe by which relatively viscous dental materials can be accurately and precisely dispensed through a very fine discharge apperture or orifice to effect a controlled deposit of the material where needed. In the various embodiments herein illustrated an improved delivery system is provided whereby efficiency and use of relatively expensive dental material can be maximized with a minimum of waste. The illustrated syringe further provides the dentist with a delivery system which can be used in a variety of dental procedures, thus greatly reducing the number and kinds of tools and implements otherwise required to perform the variety of dental procedures.

Figure 15C:
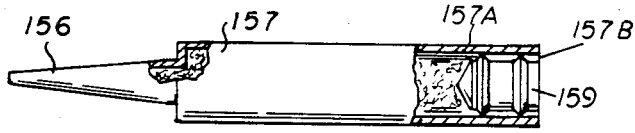
FIG. 15C is a detail view of a cartridge for use in the barrel assembly of FIGS. 15 and 15A.

FIG. 18 illustrates a modified barrel assembly which may be utilized for accommodating a cartridge construction described with respect to FIG. 15C. The barrel assembly 170 of FIG. 18 comprises an elongated tubular member 171 having an open rear end portion 172 circumscribing threads or other securing means 173 whereby it can be readily detachably connected to the barrel mount of a syringe handle 21 of FIG. 1 or handle 170 of FIG. 17. The front end of the barrel portion 171 is provided with a circumscribing end wall 175 to define a front aperture 176. Disposed intermediate to the length of the barrel 171 is an enlarged side breach opening 177. The breach opening 177 is sufficiently large so as to receive the capsule 157 as described with respect to FIG. 15C. Insertion of the cartridge 157 within the barrel 171 is effected either by inserting the cartridge 157 through the rear open end 172 or by inserting the cartridge through the side breach 177. When inserted through the side breach 177, the rear end of the cartridge 157 must be first inserted through the side opening 177 and pushed sufficiently towards the rear of the barrel so as to permit the insertion of the elongated nozzle portion 156 through the front aperture 176. If desired a disposable nozzle 166 may be inserted through the front end of the barrel 171 in advance of the cartridge 157. Thus the nozzle 166 and nozzle portion 156 provides a directional double wall nozzle arrangement to confine the material being extruded so as to permit a dentist to have directional control in depositing the material during a dental procedure. The external nozzle tip 166 further functions to confine material therein in the event of any rupture of the nozzle portion 156 during an extruding operation.

In accordance with this invention, the various barrel components, e.g. the barrel components of barrel assemblies 60, 70, 80 and 90 and their respective associated plunger tips 66, 77, 89 and 99 may be color coded so that a dentist can readily and quickly set up the syringe for a particular procedure. For example, the barrel 60, its end collar 62 and plunger tip 66 for expressing the impression material may be like colored, e.g. gold. The corresponding barrel and plunger tips for expressing an anesthesia may be colored green. The barrel components for expressing the root canal material may be colored red, etc. By color coding the respective component parts, a dentist can quickly and efficiently assemble the respective syringe components to perform a particular procedure.

It will be understood that the disposable nozzle tips, e.g. nozzle tips 65, 95, 113, 166, 127, 135, 147 and 159 are formed with a wall thickness and dispensing orifice sized necessary to express a given material depending upon the viscosity or fluidity of a given material. For example, the discharge orifice of a given tip may be sized so as to have a diameter of 1 mm to 2½mm. The wall thickness of the nozzle tips are proportioned to contain the pressures exerted thereon during an extrusion of the dental material therethrough.

Figure 13A:
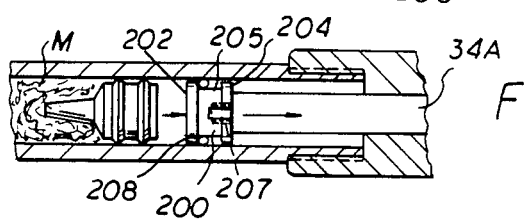
FIG. 13A is a partial sectional view of the assembly of FIG. 13, illustrating the parts in this operative position for relieving the pressure on the material.
Figure 13B:
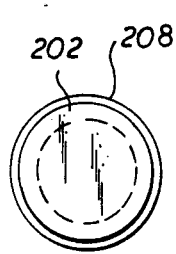
FIG. 13B is a front end view of the valve body of FIGS. 13 and 13A.
Figure 13D:
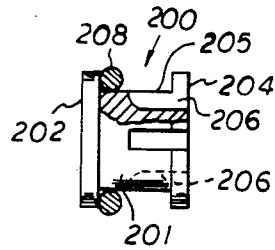
FIG. 13D is a side detail view of the valve body of FIGS. 13C and 13D.
Figure 13C:
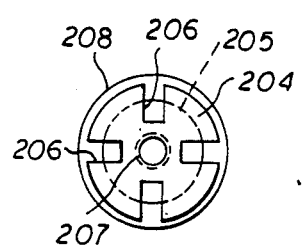
FIG. 13C is the end view of the valve body of FIGS. 13 and 13A.

FIGS. 13 to 13D illustrate another important feature of the present invention. It will be understood that the feature herein described can be utilized with any of the particular barrel assemblies herein described where there is a tendency of the material to continue to extrude out the nozzle thereof as a result of any residual pressure being imparted to the material. When a material is confined within a tube or cartridge and is dispensed therefrom by the application of pressure on the tube or cartridge, it has been noted that upon release of the pressure, a certain amount of the material will continue to extrude out therefrom due to the residual pressure acting on the confined material. To obviate this inherent loss of material from a tube or cartridge as a result of such residual pressure acting on the material, the present invention contemplates a syringe structure of the type herein described wherein the tip 37 of the plunger shaft 34A is provided with a modified plunger tip 200 which functions as a unidirectional valve means to create a vacuum on the end of the sealing plug, e.g. 139 in FIG. 13, to relieve the residual pressure which will otherwise create some unwanted extrusion of material, depending upon the virosity and pressure of the confined material.

As best seen in FIGS. 13 to 13D, the modified plunger tip 200 comprises a spool shaped member 201 having an imperforate front face 202 which has a diameter which is less than the internal diameter of the cartridge or barrel 131. Disposed between the front face 202 and a rear face 204 the spool 201 there is provided with a reduced body portion 205. The rear part of the body portion 205 and rear face 204 is provided with a series of radial passages or grooves 206, circumferentially spaced therearound. The rear face 204 is further provided with a tapped hole 207 whereby the spool body 205 can be readily threaded to the top end 37 of a plunger 34, as hereinbefore described.

Slidably disposed on the reduced body portion 205 is an O ring seal 208. The O ring seal 208 has an outer diameter which will snugly engage the internal walls of the barrel 131 and create a seal thereat. The function of the O ring 208 is such as to open the radial passages or grooves 206 as the plunger 34 is being projected into the barrel 131 to effect the evacuation of any air that may be trapped between the plug 139 and the front face 202 of the plunger tip 200 on the extruding stroke of the plunger; and to seal the grooves 206 to create a vacuum on the rear end of the plug 139 to relieve any residual pressure which may tend to act on the material in advance of the plug 131, upon the retraction of the plunger shaft 34A.

In operation, the unidirectional spool valve member 200 is threaded to the tip 37 of the plunger to define a plunger tip. The front face 202 of the plunger tip is placed in driving engagement with the rear end of the plug 139. As the plunger 34 is actuated and is projected with the barrel 131 to effect displacement of the plug 139 to extrude the material in advance thereof, the O ring 208 is forced against the rear face 204 and behind the front end of grooves 206, thus permitting any air ahead of the O ring to be exhausted to the rear of the spool member 205 through opened grooves 206. When the plunger travel has ceased, the residual pressure developed ahead of the plug 139 and acting on the material M may cause a small amount of material to continue to extrude until the pressure on the material has equalized by the expression of this small amount. As the amount and/or cost of the material may be critical in a dental procedure, the extrusion of any excess material upon the termination of the plunger advance can be controlled with the construction described, by retracting the plunger 34.

In retracting the plunger 34, e.g. to the right as viewed in FIG. 13A, the sealing friction of the O ring 208 on the walls of the barrel will cause the ring 208 to be disposed or shifted adjacent to the front end 202 of the spool 200, thus closing off grooves 206. As air is prohibited from passing seal 208 upon retraction of the plunger tip 200, a vacuum is created in the space between the plug 139 and the front face 202 of the plunger tip 200 which will effect a slight retraction of the plug 139 to thereby relieve the residual pressure which would otherwise result to expressing unwanted material from the barrel. It will be apparent that with this construction a simple and expedient solution is achieved to a sometimes disturbing problem.

It will be understood that the unidirectional plunger valve tip 200 as described may be used with any of the barrel assemblies herein described having a displaceable plug, such as plug 139, to force the material out of the barrel or cartridge upon an extruding operation.

Figure 19:
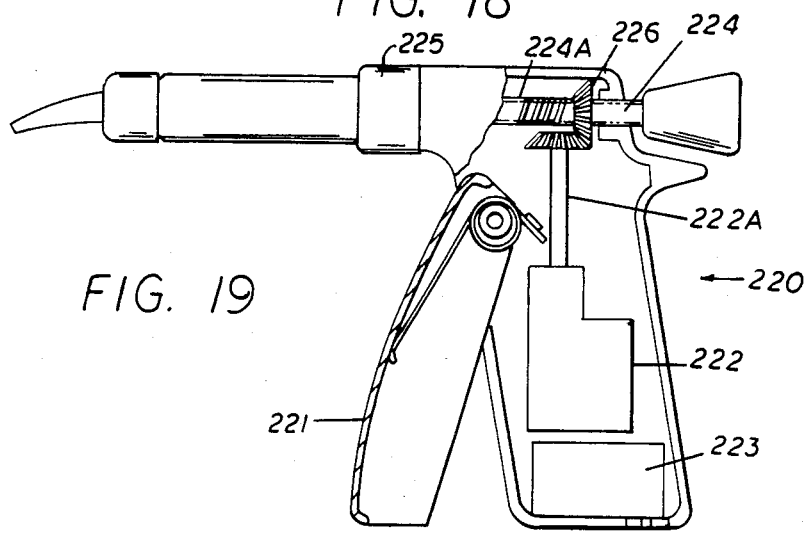
FIG. 19 is a side view of a modified power syringe handle.

FIG. 19 illustrates a modified electrically powered handle means 220 which can be readily utilized with the various barrel assemblies as hereinbefore described to define an all-purpose syringe capable of performing the various dental procedures herein set forth. In this embodiment, the power handle means or assembly 220 is defined by a pair of handle sections similar in shape as hereinbefore described. Pivotally connected between the handle section is a trigger 221 or button, which functions as a switch means to energize and/or de-energize a high torque reversible electric motor 222 mounted within or on the handle assembly. It will be understood that the power for the motor 222 may comprise a source of battery power 223 dispensed within the handle assembly 220 and/or may be connected to a conventional line current. The connection of the motor 222 in circuit with a battery source 223 renders the syringe a wholly self contained unit.

Mounted for movement within the handle assembly 220 is a plunger means 224 which is arranged to be shifted or moved in either a protracting position or retracted position. The front of the handle assembly 220 is provided with a barrel mount 225 to which the various barrel assemblies as herein described can be detachably connected thereto.

A transmission means is operatively interconnected between the motor shaft 222A and the plunger shaft 224A of the plunger means 224; whereby the rotation of the motor shaft 222A is transmitted to the plunger shaft 224A. The transmission means as shown comprises a bevel gear 225 similar to the motor shaft 222A. Bevel gear 325 intermeshes with a ring worm gear 226 rotatably journaled within the handle assembly.

The shaft 224A of the plunger means 224 is provided with an external worm screw which extends through and meshes with the worm threads of the ring worm gear 226. The arrangement is such that upon the actuation of the motor 222, the rotation of its shaft 222A is transmitted to the plunger shaft 224A to either advance it into the connected barrel assembly or to retract the plunger shaft depending upon the direction of rotation of the motor 222. The direction of rotation of the motor can be controlled by a two position handle means and/or by a proper selector means which will arrange the circuit to effect either a forward drive or a reverse or retraction drive for the plunger shaft.

In all other respects, the function and operations of the electric power handle 220 and associated barrel assemblies is similar to that herein described with respect to FIG. 1.

In the arrangement described, e.g. in the syringe 20 of FIG. 1, the plunger 34 is manually retracted, first by rotating the plunger shaft to disengage the ratchet teeth from the ratchet pawl 41A; and then retracting the plunger 34. When the plunger 34 has been fully retracted, the holding pawl with engage the stop groove 38, and thereby prohibit any unintentional removal or separation of the plunger shaft from the handle 21. However, if the dentist wishes to intentionally separate or remove the plunger from the handle, e.g. for cleaning or to change the plunger tip or for whatever reason, it can be readily removed by setting the adjusting button 51 to the highest or A position as seen in FIG. 3, and pushing the trigger upwardly slightly. In doing so, the shoulder 32 of the trigger will effect a slight displacement of the holding cam 38 sufficient to disengage it from the stop groove 38 which will permit removal of the plunger 34 from the handle. Thus, the components described can be readily separated, but not by accident or without intention.

While the syringes herein described have particular application in dentistry, they have application in certain medical surgical procedures as herein described. Also, the syringes described may be used in industry to precisely control the deposits of industrial materials such as glues, epoxies and other adhesives and/or fillers.

The present invention further contemplates a syringe construction in which the component barrel position may also function as the container or cartridge in which the dental material may be sold or packaged, and from which the material can be readily dispensed as required. Also due to the viscosity of certain materials, a power handle is provided whereby a sufficient mechanical advantage is achieved to extrude a viscous material through relatively small and minute passages with considerable ease; and whereby the pressure imparted on the material can be relieved to prohibit any excess extrusion of the material, subsequent to an extruding operation.

While the invention has been described with respect to certain embodiments thereof, it will be understood and appreciated that variations and modifications may be made within the scope and spirit of the invention.

What is claimed is:

1. An expendible bulk dispensing cartridge for both packaging a dental material and for dispensing a plurality of variable proportions of the dental material contained therein directly to the tooth cavity in different patients without cross contamination, comprising an elongated tubular member formed of a light opaque plastic material and having a reservoir portion, said reservoir portion extending throughout a major portion of said tubular member, said tubular member having a full open end portion at one end thereof, and a nozzle connected to the other end of said tubular member and said nozzle being integrally formed with said reservoir portion, said tubular member having means for connecting to a syringe handle, a bulk supply of light curable dental material, for use on more than one patient disposed in said reservoir portion, an end plug sealing the full open end of said tubular member for confining said dental material within said reservoir portion, said end plug being displaceably disposed within said tubular member whereby the displacement of said plug effects the extrusion of said material through said nozzle, a readily disposable discharge tip, means for detachably connecting said disposable tip to said nozzle, and permitting said disposable tip to be rotated relative to said nozzle 360° for directional control in dispensing said material, said disposable tip extending beyond the end of said nozzle whereby said nozzle is encased wholly within said disposable tip to prohibit any contact between said nozzle and the tooth being filled, said disposable tip having an angularly disposed discharge opening relative to the longitudinal axis of said tubular member, and a cap for sealing the end of said nozzle when said cartridge is not in use.

* * * * *